United States Patent
Ho et al.

(10) Patent No.: US 9,884,180 B1
(45) Date of Patent: Feb. 6, 2018

(54) POWER TRANSDUCER FOR A RETINAL IMPLANT USING A CONTACT LENS

(71) Applicants: Harvey Ho, Mountain View, CA (US); Babak Amirparviz, Mountain View, CA (US)

(72) Inventors: Harvey Ho, Mountain View, CA (US); Babak Amirparviz, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 700 days.

(21) Appl. No.: 13/627,548

(22) Filed: Sep. 26, 2012

(51) Int. Cl.
  *A61N 1/36* (2006.01)
  *A61N 1/05* (2006.01)
  *A61N 1/378* (2006.01)

(52) U.S. Cl.
  CPC ....... *A61N 1/0543* (2013.01); *A61N 1/36046* (2013.01); *A61N 1/3787* (2013.01)

(58) Field of Classification Search
  None
  See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Bionic contact lens 'to project emails before eyes,' http://www.kurzweilai.netforums/topic/bionic-contact-lens-to-project-emails-before-eyes, Last accessed Mar. 14, 2012, 2 pages.

(Continued)

*Primary Examiner* — Erica Lee
(74) *Attorney, Agent, or Firm* — McDonnell Boehnen Hulbert & Berghoff LLP

(57) ABSTRACT

Apparatus, systems and methods employing contact lens as power source for powering a retinal implant are provided. In an aspect, a contact lens includes a substrate that forms at least part of a body of the contact lens and a circuit disposed on or within the substrate comprising. The circuit includes a power harvesting component configured to receive energy in a first form from an external power source and convert the energy from the first form to a second form and an energy transfer component configured to transmit the energy in the second form to device remote from the contact lens when the contact lens is worn over an eye.

14 Claims, 7 Drawing Sheets

(56) References Cited

U.S. PATENT DOCUMENTS

| | | |
|---|---|---|
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,935,155 A * | 8/1999 | Humayun et al. ............ 607/54 |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 * | 5/2003 | Goldstein ............ 324/415 |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0106965 A1 * | 6/2004 | Chow ............ 607/54 |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0179552 A1 * | 8/2007 | Dennis ............ A61N 1/056 607/37 |
| 2007/0188710 A1 | 8/2007 | Hetling et al. |
| 2008/0208335 A1 * | 8/2008 | Blum ............ A61F 2/1616 623/6.22 |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1 * | 4/2010 | Amirparviz ...... B29D 11/00826 351/158 |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2010/0280417 A1 * | 11/2010 | Skelton ............ A61M 5/14276 600/595 |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |

(56) References Cited

U.S. PATENT DOCUMENTS

| | | | |
|---|---|---|---|
| 2012/0092612 | A1 | 4/2012 | Binder et al. |
| 2012/0109296 | A1 | 5/2012 | Fan |
| 2012/0111339 | A1* | 5/2012 | Barthe .................... A61N 7/00 128/846 |
| 2012/0177576 | A1 | 7/2012 | Hu |
| 2012/0201755 | A1 | 8/2012 | Rozakis et al. |
| 2012/0245444 | A1 | 9/2012 | Otis et al. |
| 2012/0259188 | A1 | 10/2012 | Besling |
| 2012/0271121 | A1* | 10/2012 | Della Torre ......... A61B 5/0059 600/301 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 1995/004609 | 2/1995 |
| WO | 2001/016641 | 3/2001 |
| WO | 2001/034312 | 5/2001 |
| WO | 2003/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-µW CMOS Glucose Sensor for Wireless Contact-Lens Tear Glucose Monitoring," IEEE Journal of Solid-State Circuits, Jan. 2012, pp. 335-344, vol. 47, No. 1.

Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh, et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

(56) References Cited

OTHER PUBLICATIONS

Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

\* cited by examiner

POWER TRANSDUCER FOR A RETINAL IMPLANT USING A CONTACT LENS

TECHNICAL FIELD

This disclosure generally relates to a contact lens having a power transducer integrated therein or thereon for providing power to a retinal implant.

BACKGROUND

A retinal implant is a biomedical device used to restore useful vision to individuals that have lost vision due to degenerative eye conditions such as retinitis pigmentosa or macular degeneration. Retinal implants provide low resolution images by electrically stimulating retinal cells. Such images may be sufficient for restoring specific visual abilities, such as light perception and object recognition.

Retinal implants are surgically implanted into the eye of an individual and are intended to remain in place for long periods of time, so long as the implant operates properly. However, retinal implants are difficult to power. Due to their limited lifetime, batteries as a power source for retinal implants unavoidably leads to surgical removal and replacement of implants; a processes that is costly and cumbersome to the patient. Moreover, batteries add bulkiness and weight to a retinal implant; can cause adverse physical reactions in response to battery leakage or corrosion.

DETAILED DESCRIPTION

Figure 1:
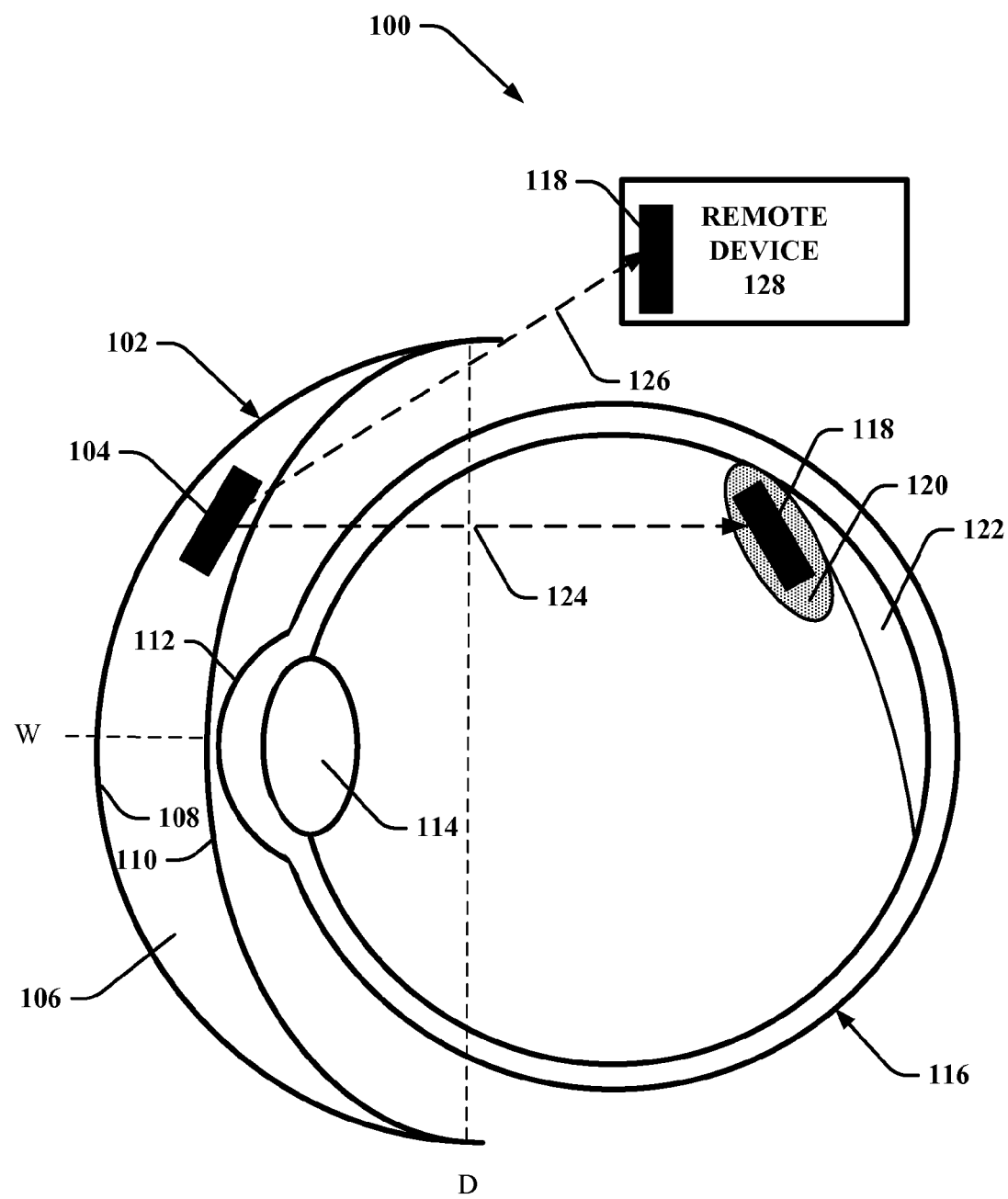
FIG. 1 illustrates an example system employing a contact lens to provide power to an external device, including a retinal implant, in accordance with aspects described herein.

In one or more aspects, the disclosed subject matter relates to a contact lens having a power transducer integrated therein or thereon for providing power to another device. In an aspect, the contact lens includes a substrate that forms at least part of a body of the contact lens and a circuit disposed on or within the substrate. The circuit can include a power harvesting component configured to receive energy in a first form from an external power source and convert the energy from the first form to a second form, and an energy transfer component configured to transmit the energy in the second form to a device remote from the contact lens when the contact lens is worn over an eye. In various aspects, the remote device is a retinal implant integrated on or within part of the eye. In an aspect, the power harvesting component can include one or more solar power cells configured to capture solar energy and convert the solar energy to radio frequency energy. The energy transfer component can then transmit the radio frequency energy to the device.

In addition, a method is disclosed that includes receiving at a contact lens worn over an eye, energy in a first form from an external power source, converting the energy from the first form to a second form using a transducer disposed on or within the contact lens, and transmitting the energy in the second form to a device remote from the contact lens using an energy transfer component disposed on or within the contact lens. In various aspects, the remote device is a retinal implant integrated on or within part of the eye. In an aspect, the converting includes converting the energy in the first form to radio frequency energy, and the transmitting includes transmitting the radio frequency energy to the remote device using a radio frequency antenna disposed on or within the contact lens.

In another embodiment, a system is disclosed that includes a retinal implant configured to implant on or within an eye and a contact lens configured to provide power to the retinal implant when worn over the eye. In an aspect, the retinal implant includes a substrate configured to contact a surface of a retina of the eye and a circuit disposed on or within the substrate. The circuit can include a receiver configured to wirelessly receive energy in a first form from the contact lens; and a transducer configured to convert the energy in the first form to energy in a second form. The retinal implant employs the energy in the second form to power operations of the retinal implant. In an aspect, the receiver includes a radio frequency antenna configured to receive the energy in the first form as radio frequency energy.

Various aspects are now described with reference to the drawings, wherein like reference numerals are used to refer to like elements throughout. It should be appreciated that one or more aspects of the drawings from are not drawn to scale. In the following description, for purposes of explanation, numerous specific details are set forth in order to provide a more thorough understanding of one or more aspects. It should be evident, however, that such aspects can be practiced without these specific details. In other instances, structures and devices are shown in block diagram form in order to facilitate describing one or more aspects.

With reference now to the drawings, FIG. 1 illustrates a system 100 for powering a device remote from a contact lens using power provided by the contact lens. In an aspect system 100 employs a contact lens 102 to generate and provide power 124 to a retinal implant 120 disposed on or within an eye 116. With system 100, retinal implant 120 can operate without an internal power source (e.g. a battery) and/or without a wired connection to an external power source.

Contact lens 102 can also be used to power other devices 128 aside from a retinal implant. For example, contact lens 102 can be used to provide power to another biomedical device associated with the individual wearing contact lens 102 or a non-biomedical device associated with the individual. Accordingly, system 100 further depicts contact lens 102 providing power 126 to another remote device 128. It should be appreciated that although system 100 depicts contact lens 102 providing power to both retinal implant 120 and remote device 128, system 100 can include a contact lens 102 providing power to a single device (e.g. either retinal implant 120 or remote device 128). In other aspects, system 100 can include a contact lens 102 providing power to N devices N (where N is an integer).

System 100 includes a contact lens 102 that is worn over an eye 116. Contact lens 102 includes a circuit 104 disposed on or within a substrate 106. In an aspect, the substrate 106 is a hydrogel—however, contact lenses disclosed herein can include any suitable material. In an aspect, the contact lenses disclosed herein can include soft lenses made from one or more soft polymer materials including but not limited to, a hydrogel, a silicone based hydrogel, a polyacrlyamide, or a hydrophilic polymer. For example, in an aspect, contact lenses disclosed herein can include crosslinked hydrogels including hydrophilic monomers (e.g. N-Vinylpyrrolidone, N,N-dimethylacrylamide, 2-hydroxyethyl methacrylate, hydroxyethyl acrylate, methacrylic acid and acrylic acid), strengthening agents, ultraviolet light (UV) blockers, or tints. In another aspect, contact lenses disclosed herein can include silicone hydrogels (e.g. crosslinked hydrogels containing silicone macromers and monomers, as well as hydrophilic monomers that absorb water). In yet another aspect, contact lenses disclosed herein can include hard lenses made from one or more rigid materials including but not limited to, a silicone polymer, polymethyl methacrylate, or rigid gas permeable materials.

Although not to be limited to such shape, contact lenses disclosed herein, such as contact lens 102, are generally provided in a spherical shape that conforms to shape of an eye. With reference to FIG. 1, contact lens 102 includes two primary surfaces, an inner surface 110 and an outer surface 108, both of which are spherical. The inner surface 110 is concave and is shown facing and resting on a surface of the eye 116, and conforming to shape of the eye 116—the outer surface 110 is convex. (Although contact lens 102 is drawn not directly resting/contacting eye 116, it is to be appreciated that contact lens 102 rests on eye 116 in spirit.)

Contact lens circuit 104 can have any suitable size and shape that allows for inclusion of circuitry and various components that facilitate receipt of external power, processing of the power, and transmission of the power, without irritating the eye, without disrupting functions of the eye or the contact lens, and without causing discomfort to the wearer. Contact lens 102 (and additional contact lenses described herein) has a thickness or width that spans in a horizontal direction between inner surface 110 and outer surface 108. Dashed line W indicates direction of the width or depth of the contact lens 102. Diameter of the contact lens 102 is indicated by dashed line D. The particular dimensions (including dimensions attributable to thickness, diameter, curvature, and etc.) of the subject contact lenses are not critical and can vary. One or more components of contact lens circuit 104 can be located throughout the thickness of the contact lens substrate 106, suspended within a thickness of the substrate, and/or adjacent to an inner 110 or outer surface 108 of the contact lens 102. In various aspects, contact lens circuit 104 is disposed within the substrate so as to not interfere/overlap with a visual region of the eye (e.g. the pupil/iris).

Contact lens circuit 104 can include various electrical components that facilitate energy harvesting and wireless energy transfer. In an aspect, circuit 104 includes a power harvesting component (not shown) configured to receive energy in a first form from an external power source (e.g. solar power from sunlight) and convert the energy from the first form to a second form (e.g. radio frequency energy). According to this aspect, the power harvesting component functions as a transducer. The circuit 104 can further include an energy transfer component (not shown) configured to transmit the energy in the second form to a device remote from the contact lens. In particular, in system 100, circuit 104 wirelessly transmits energy (e.g. energy 124 and/or energy 126) to a retinal implant 120 that is located on or within an eye 116 over which contact lens 102 is worn and/or another remote device 128. Contact lens circuit 104 is described in greater detail with respect to FIG. 2.

A retinal implant is a biomedical device used to restore useful vision to people who have lost their vision due to degenerative eye conditions such as retinitis pigmentosa or macular degeneration. Retinal implants provide people with low resolution images by electrically stimulating retinal cells. Such images may be sufficient for restoring specific visual abilities, such as light perception and object recognition. In some aspects retinal implants are placed on or within the retina (e.g. epiretinal implants). In other aspects, retinal implants are implanted behind the retina (subretinal implants) and placed between the outer retinal layer and the retinal pigment epithelium.

As seen in FIG. 1, eye 116 is depicted with a few basic anatomical features to facilitate presentation of how a contact lens (e.g. 102) is generally worn over an eye and to demonstrate an implanted retinal implant 118. Eye 116 includes a cornea 112, a lens 114, and a retina 122. It should be appreciated that that contact lens 102, eye 116 and the physical components of eye 116 are not drawn to scale. Retinal implant 120 is implanted within the body of the eye in front of the retina 122. In an aspect, the retinal implant 120 includes a substrate configured to contact a surface of the retina 122 of the eye 116 and at least a circuit 118 to facilitate operation of the retinal implant. It should be appreciated that placement of the retinal implant within the eye is not critical to system 100. For example, in some aspects, retinal implant 118 can be implanted behind the retina 118 and/or outside of eye 116.

Retinal implant 120 and remote device 128 respectively include at least a circuit 118 that facilitates powering the respective devices. Circuit 118 includes a receiver (not shown) configured to wirelessly receive energy in a first form from contact lens 102. The circuit 118 can further include a transducer configured to convert the energy in the first form to energy in a second form. The respective devices (e.g. device 118 and device 128) can further employ the energy received from contact lens 102 to power operations of the respective devices. Circuit 118 is described in greater detail with respect to FIG. 3.

Figure 2:
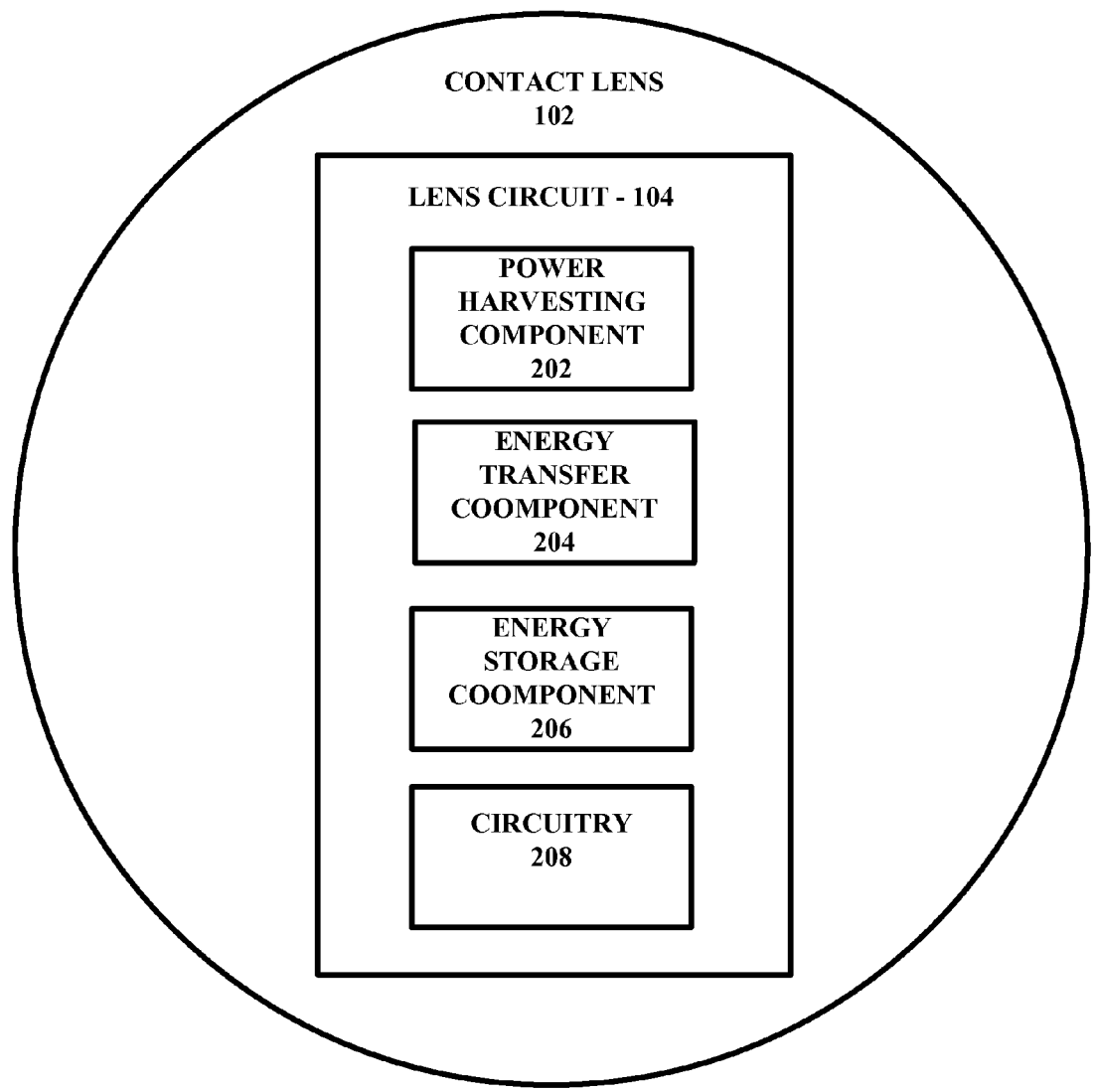
FIG. 2 presents a high level block diagram of an example contact lens for providing power to an external device in accordance with aspects described herein.

Turning now to FIG. 2, presented is a high level illustration of an example contact lens that facilitates gathering, processing and wirelessly transmitting energy in accordance with aspects described herein. Repetitive description of like elements employed in respective embodiments of contact lenses and contact lens circuits described herein is omitted for sake of brevity.

As shown in FIG. 2, contact lens 102 includes a contact lens circuit 104. Contact lens circuit 104 can include power harvesting component 202, energy transfer component 204, energy storage component 206, and circuitry 208. In various aspects, one or more of the power harvesting component 202, energy transfer component 204, energy storage component 206, and circuitry 208, are electrically coupled to one another to perform one or more functions of the contact lens circuit 104. For example, one or more wires can connect the various components of contact lens circuit 104.

As discussed above, contact lens circuit 104 includes power harvesting component 202 is configured to receive energy in a first form from an external power source and convert the energy from the first form to a second form.

Power harvesting component 202 include suitable circuitry that facilitates gathering or receiving the energy in the first form (e.g. solar, mechanical, thermal, acoustic, chemical, or RF) and converting the energy into a second form, (e.g. usable energy and/or transferable energy). Accordingly, power harvesting component 202 functions in part as a transducer.

In a primary embodiment, power harvesting component 202 harvests solar energy (e.g. light/sunlight). With this embodiment, power harvesting component 202 can include one or more photovoltaic (e.g. solar) cells disposed on or within the substrate of the contact lens 102. The one or more solar cells are configured to receive incident light and convert the light energy into an electrical signal that can be employed to power a device. For example, contact lens 102 can include one or more solar cells disposed on or near an outer surface of the lens. The one or more solar cells can receive incident sunlight and convert the sunlight into an electrical power, such as a direct current (DC).

The one or more solar cells of energy harvesting component 202 can include various suitable light absorbing materials that facilitate integration on or within contact lens 102. For example, a solar cell can include at least one of: silicon (e.g. silicon in a thin film form), amorphous silicon, crystalline silicon, (including monocrystalline silicon and polycrystalline silicon), cadmium telluride, or copper indium selenide/sulfide.

In other embodiments, power harvesting component 202 can harvest energy from other types of external sources in addition to or in the alternative of solar energy. In particular, power harvesting component 202 can be configured to harvest various forms of energy including but not limited to: mechanical energy, thermal energy, acoustic energy, or chemical energy. For example, power harvesting component 202 can include a mechanically derived power source (e.g., a MEMs system) configured to harvest energy generated in response to body movement, eye movement, eyelid movement. In another example, energy harvesting component 202 can include a device that converts body heat and/or external heat into usable energy.

In some aspects, power harvesting component 202 is configured to harvest external radio frequency (RF) energy. According to this aspect, energy harvesting component can include a receiver or transceiver (e.g. an RF antenna) configured to receive emitted RF power. In some aspects, the emitted RF power can be intentionally emitted to contact lens 102 from an external device. In another other aspects, energy harvesting component 202 can be configured to harvest ambient RF energy present in the environment. The energy harvesting component 202 can then either convert the received RF energy into usable energy, store the energy, and/or provide the RF energy to energy transfer component 204 for transfer of the energy to another device remote from contact lens 102 (e.g. a retinal implant).

In various aspects, energy harvesting component 202 can harvest energy from two or more external energy sources. For example, energy harvesting component can employ both a solar cell and a MEMs system for harvesting solar energy and mechanical energy respectively. According to this aspect, energy harvesting component can pool energy received from various external sources.

Regardless of the source of the energy, energy harvesting component 202 receives or generates energy that can be employed to power various components of contact lens 102, stored in an energy storage component 206, and/or transmitted to another device. Energy storage component 206 can include any suitable power storage component configured to store power. For example, energy storage component 206 can include a battery or a capacitor. In some aspects, contact lens 202 can include energy storage component 202 as a means to store energy received and/or generated by contact lens circuit 106. In other aspects, contact lens 202 includes energy storage component 206 as a source of internal energy that can be used to power components of contact lens 102 and/or that can be employed to transmit power to an external device.

However, in other aspects, contact lens 102 does not include an energy storage component 206. According to these aspects, contact lens 102 directly employs energy generated by power harvesting component 202 and/or transmits the energy to another device (e.g. a retinal implant) using energy transfer component 204.

Energy transfer component 204 is configured to transmit energy from contact lens 102 to another device remote from contact lens 102. In an aspect, energy transfer component 204 is configured to transmit energy received by and/or generated by power harvesting component 204. In another aspect, energy transfer component 204 is configured to transmit energy stored in energy storage component 206 to an external device.

Energy transfer component 204 can include suitable hardware components that facilitate transmission of wireless energy in various forms. In an embodiment, energy transfer component 204 transmits energy from contact lens 102 to anther device (e.g. a retinal implant) as RF energy. According to this embodiment, energy transfer component can include a transmitter, such as an RF antenna, configured to transmit RF energy from contact lens 102 to a remote device. In particular, power harvesting component 202 and/or energy transfer component 204 can convert power received or stored at contact lens 102 to RF energy and energy transfer component 204 can transmit the RF energy to a remote device using an RF transmitter. For example, power harvesting component 202 can generate a direct current from solar energy (e.g. using one or more solar cells) and/or mechanical energy (e.g. using a MEMs device). The power harvesting component 202 or the energy transfer component can then convert the direct current into radio frequency energy using a DC/RF converter. The energy transfer component 206 can then transmit the RF energy to an external device using an RF antenna.

It should be appreciated that the precise circuit configuration for converting external energy to RF energy and transmitting the RF energy to an external device by contact lens circuit 104 can vary and is not critical to the general purpose of circuit 104. For example, in some aspects, power harvesting component 202 and energy transfer component 204 can share various circuit hardware. For example, in an aspect, power harvesting component 202 and energy transfer component 204 can be embodied in a transceiver configured to receive external RF energy and relay the external RF energy to another device (e.g. a retinal implant).

In another embodiment, energy transfer component 204 can include an induction coil configured to transfer energy from contact lens 102 as an evanescent wave. According to this embodiment, energy transfer component 204 can wirelessly transmit energy from contact lens 102 using direct induction or resonant magnetic induction. For example, energy transfer component 204 can employ energy generated by power harvesting component 202 (e.g. DC power) and/or stored by energy storage component 206 to cause a primary induction coil to resonate a predetermined frequency matching a receiving induction coil provided in an external device, thereby causing energy to transfer from the primary induction coil to the secondary induction coil.

It should be appreciated that contact lens circuit 104 can further include the appropriate circuitry 208 to facilitate functions of contact lens circuit 204. For example, circuitry 208 can include various hardware that facilitates operation of power harvesting component 202, energy transfer component 204 and/or energy storage component 206. For example, circuitry can include power converters, rectifiers, filters, and/or amplifiers. In an aspect, circuitry (associated with power harvesting component 202 and/or energy transfer component 204) includes an RF power amplifier configured to amplify an RF signal for transmission to a remote device (e.g. a retinal implant).

Figure 3:
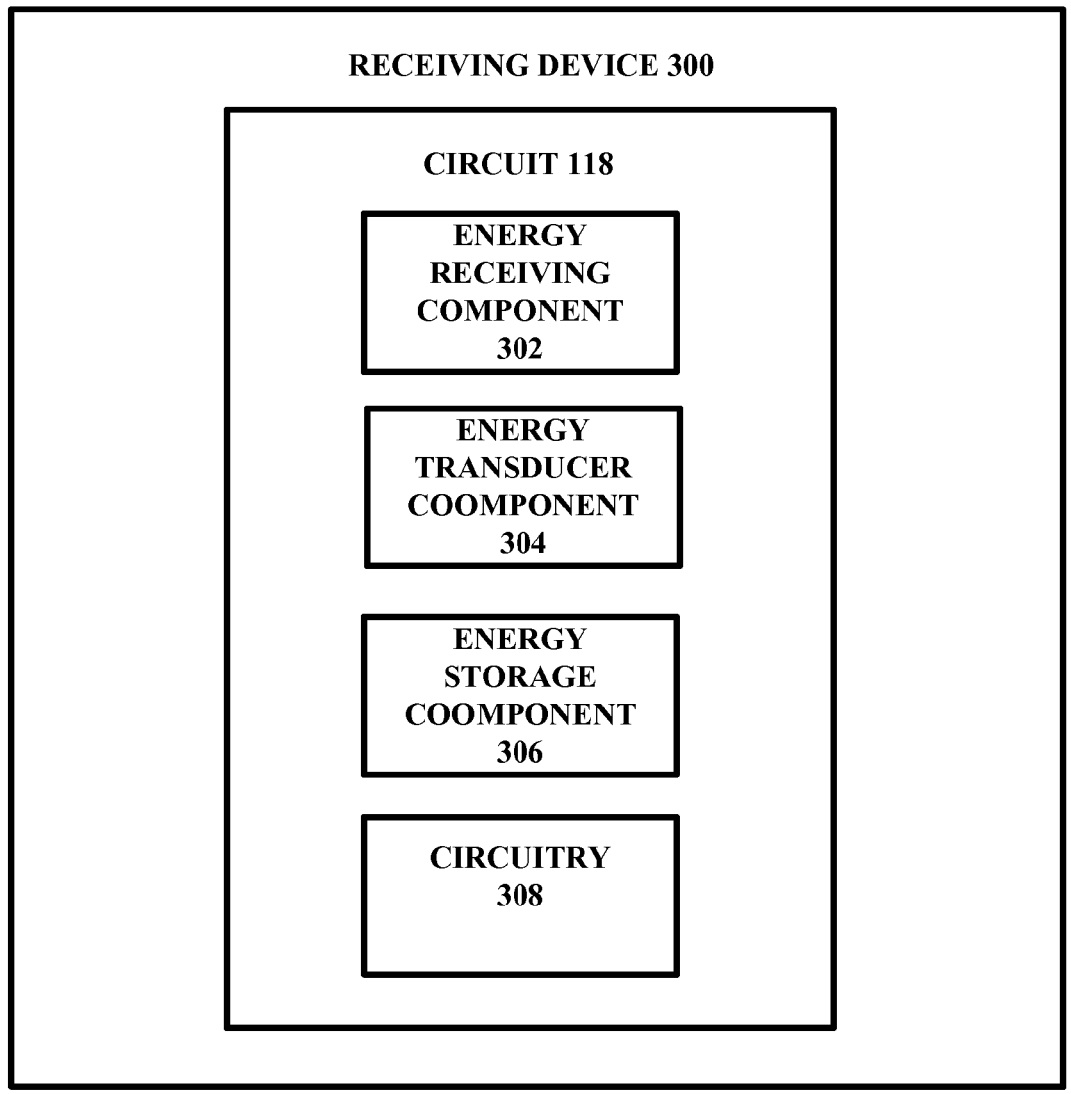
FIG. 3 presents a high level block diagram of an example receiving device for receiving power from a contact lens in accordance with aspects described herein.

Referring now to FIG. 3, presented is a high level illustration of an example receiving device 300 configured to wirelessly receive energy transmitted from a contact lens in accordance with aspects described herein. In various aspects, receiving device 300 can include one or more of the structure and/or functionality of retinal implant 120 or remote device 128 (and vice versa). Repetitive description of like elements employed in respective embodiments of contact lenses, contact lens circuits, and receiving devices (e.g. a retinal implant or other remote device) described herein is omitted for sake of brevity.

Receiving device 300 can include a device configured to receive wireless power transferred from a contact lens (e.g. contact lens 102 as disclosed herein) and employ the received power to power operations of the device. In an aspect, receiving device 300 is a retinal implant, such as retinal implant 120. In another aspect, receiving device 300 is another biomedical device worn by an individual who wears a contact lens 102. For example, receiving device 300 can include a cochlear implant or drug delivery device. Still, in other aspects, the receiving device can include a non-medical device.

As shown in FIG. 3, receiving device 300 includes circuit 118 configured to facilitate wireless energy transfer to receiving device 300 from a contact lens (e.g. contact lens 102). Circuit 118 can include energy receiving component 302, energy transducer component 304, energy storage component 306, and circuitry 308. In various aspects, one or more of the energy receiving component 302, energy transducer component 304, energy storage component 306, and circuitry 308, are electrically coupled to one another to perform one or more functions of the contact lens circuit 118. For example, one or more wires can connect the various components of circuit 118.

Energy receiving component 302 is configured to wirelessly receive energy in a first form from a contact lens worn over an eye of an individual. In an aspect, energy receiving component 302 includes an RF receiver, such as an RF antenna, configured to receive the energy in the first form as RF energy. In another aspect, the energy receiving component 302 includes an induction coil configured to receive energy from a contact lens via direct induction or resonant magnetic induction. According to this aspect, the induction coil can be configured to resonate at a same frequency as a primary induction coil provided within the contact lens and receive energy transferred from the primary induction coil as an evanescent wave.

Energy transducer component 304 is configured to convert energy received at energy receiving component 302 into usable energy for powering operations of the device 300. In an aspect, energy transducer component includes a power converter configured to convert RF energy into usable DC power. In another aspect, energy transducer component 304 is configured to convert magnetic energy (e.g. induction based energy induced in an induction coil of the energy receiver component 302) into a voltage current or DC power. The DC power generated by the energy transducer component can be employed by device 300 to facilitate operations of the device and/or stored in energy storage component 306 for future use.

Energy storage component 306 can include any suitable power storage component configured to store power. For example, energy storage component 306 can include a battery or a capacitor. In an aspect, receiving device 300 can include an energy storage component to store energy received from a contact lens for later use. In another aspect, receiving device 300 can employ energy transfer from a contact lens as a means to recharge energy storage component 306. According to this aspect, energy storage component 306 can include a rechargeable power source.

However, in a primary embodiment, receiving device 300 does not include an energy storage component 306. In particular, receiving device 300 can operate solely on power transferred thereto from a contact lens (e.g. contact lens 102). For example, when receiving device 300 is a retinal implant, the retinal implant can operate without a battery using energy transferred from a contact lens. Circuit 118 can further include the appropriate circuitry 308 to facilitate functions of the circuit. For example, circuitry 308 can include hardware that facilitates operation of energy receiving component 302, energy transducer component 304, and/or energy storage component. For example, circuitry 308 can include power converters, rectifiers, filters, and/or amplifiers.

Referring now to FIGS. 4A-4D, depicted are top planar views of various example contact lenses configured to provide wireless power to a remote device in accordance with aspects described herein. In each of FIGS. 4A-4D, a contact lens 402 is exemplified when worn over an eye 404. Repetitive description of like elements employed in respective embodiments of contact lenses and contact lens circuits described herein is omitted for sake of brevity.

Figure 4B:
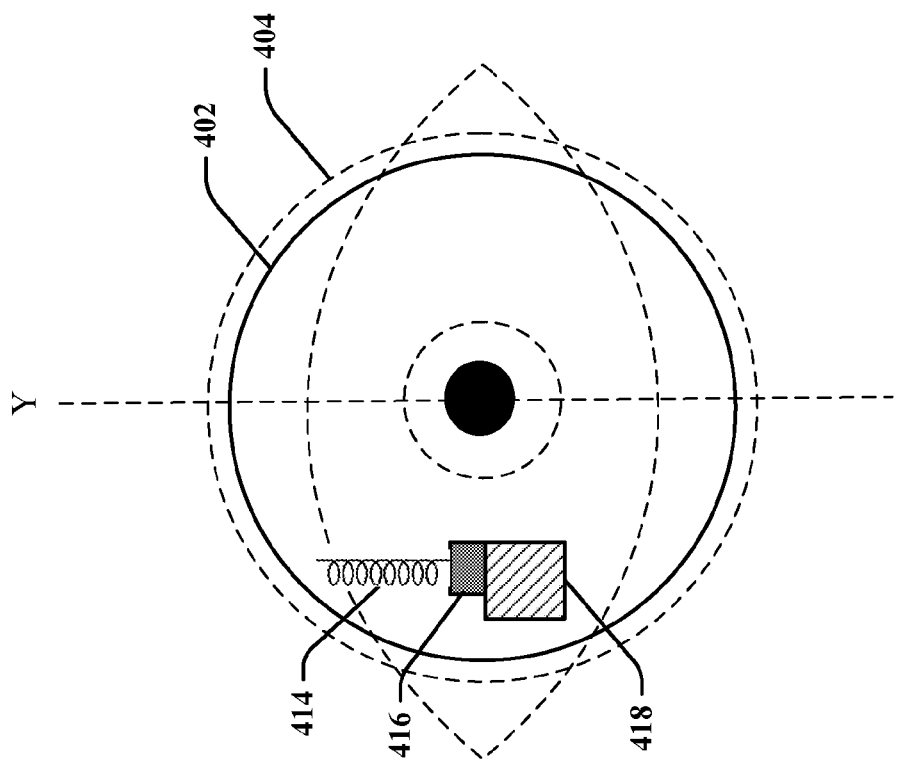
FIG. 4A-4D illustrate top planar views of examples contact lenses configured to harvest energy from an external data source and provide the energy to an external device, in accordance with aspects described herein.
Figure 4A:
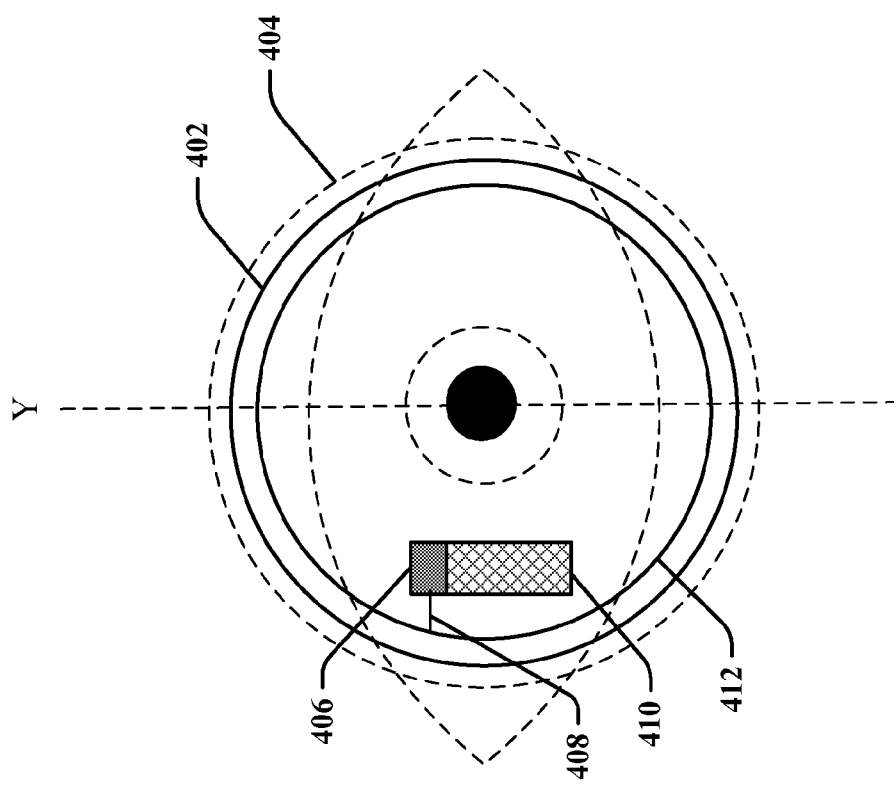

With reference initially to FIG. 4A, presented is a top-planar view of an example contact lens 402 in accordance with disclosed aspects. Contact lens 402 includes a solar panel array 410 that includes one or more photovoltaic cell configured to receive incident light and convert the incident light to an electric current, such as a direct current. Contact lens 402 can include circuitry 406 to facilitate conversion of a current (e.g. a DC current) generated by the solar panel array 410 into one or more RF waves. Contact lens 402 further includes an antenna 412 configured to transmit the one or more RF waves to a remote device such as a retinal implant. One or more wires 408 can connect circuitry 406 and/or solar panel array 410 with antenna 412. In an aspect, as depicted in FIG. 4A, the antenna 412 is disposed as a circular ring around a perimeter of contact lens 402. However, antenna 412 can have any suitable size, shape and disposition on or within contact lens 402.

FIG. 4B presents another top-planar view of an example contact lens 402 in accordance with disclosed aspects. Contact lens 402 includes MEMs device 418 configured to receive mechanical energy generated in response to body movement, including eye movement and eyelid movement, and convert the mechanical energy into an electric current, such as a direct current. Contact lens 402 can include circuitry 416 to facilitate processing of a current generated by MEMs device 418 for powering a primary inductance coil 414. In particular, circuitry 416 can apply a voltage to primary inductance coil such that the coil 414 resonates at a predetermined frequency as a secondary inductance coil disposed in a remote device thereby facilitating electromagnetic inductance energy transfer from the primary coil to the secondary coil.

Figure 4D:
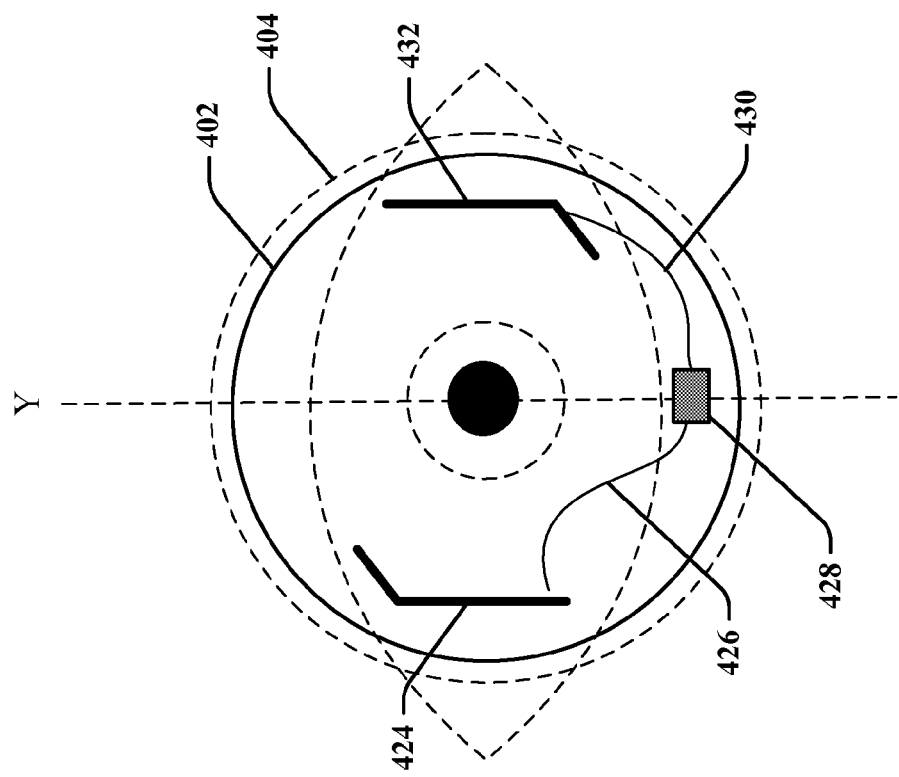
Figure 4C:
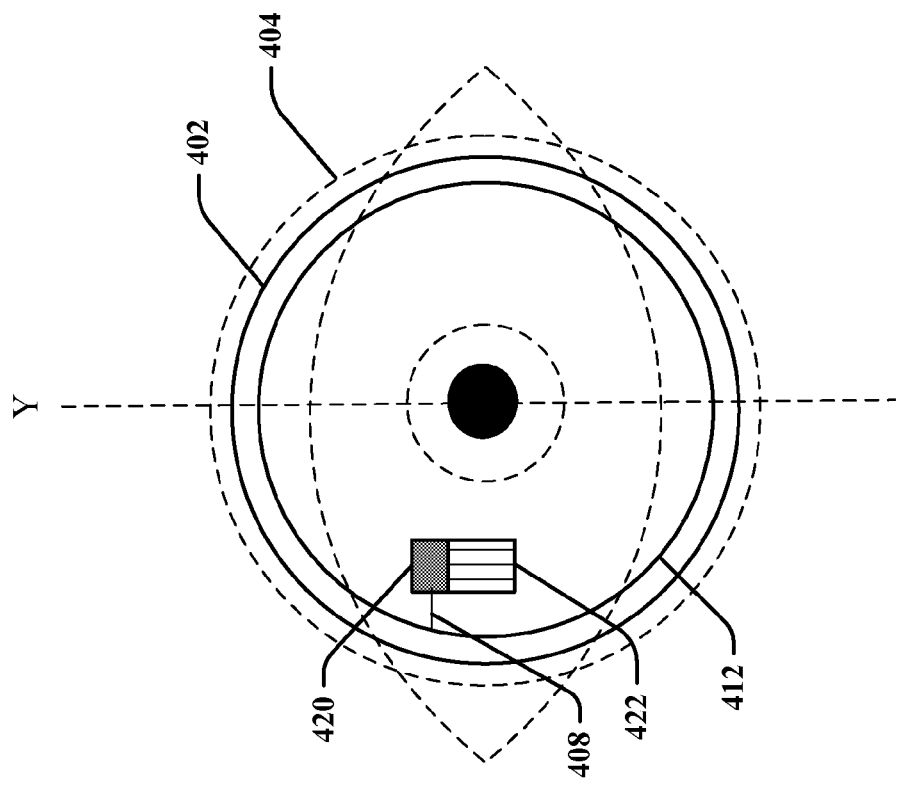

FIG. 4C depicts another top-planar view of an example contact lens 402 in accordance with disclosed aspects. Contact lens 402 includes an energy storage device 422, such as a battery or capacitor, configured to store energy. Contact lens 402 can include circuitry 420 to facilitate conversion of energy stored in energy storage device 422 into one or more RF waves. Contact lens 402 further includes an antenna 412 configured to transmit the one or more RF waves to a remote device such as a retinal implant. One or more wires 408 can connect circuitry 420 and/or energy storage device 420 with antenna 412. In an aspect, as depicted in FIG. 4C, the antenna 412 is disposed as a circular ring around a perimeter of contact lens 402. However, antenna 412 can have any suitable size, shape and disposition on or within contact lens 402.

FIG. 4D illustrates another top-planar view of an example contact lens 402 in accordance with disclosed aspects. Contact lens 402 include a receiver 424 configured to receive external RF energy. In some aspects, the external RF energy is intentionally transmitted to contact lens 402. In other aspects, the external RF energy can include ambient RF energy present in the environment. Contact lens 402 can further include circuitry 428 to facilitate processing of the received RF energy. For example, circuitry can include one or more filters and/or amplifiers configured to amplify received RF energy and convert the RF energy into a radio wave having a predetermined frequency. Contact lens 402 further includes transmitter 432 configured to transmit the received and/or processed RF energy to a remote device, such as a retinal implant. One or more wires 426 and 430 can connect receiver 424 and transmitter 432 to circuitry 428, respectively.

Figure 5:
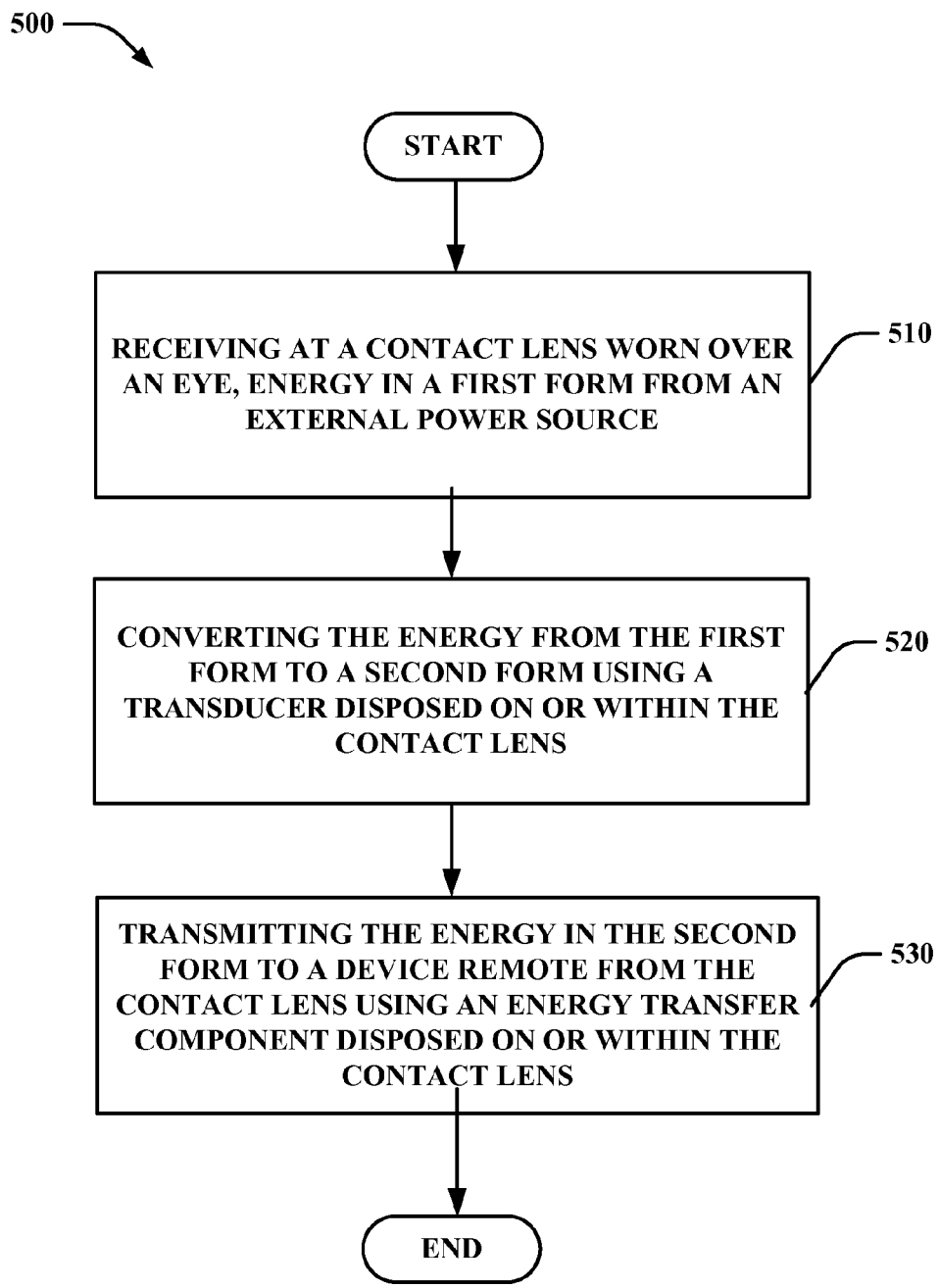
FIG. 5 is an exemplary flow diagram of a method for harvesting energy from an external data source using a contact lens and transmitting the energy to another device in accordance with aspects described herein.
Figure 6:
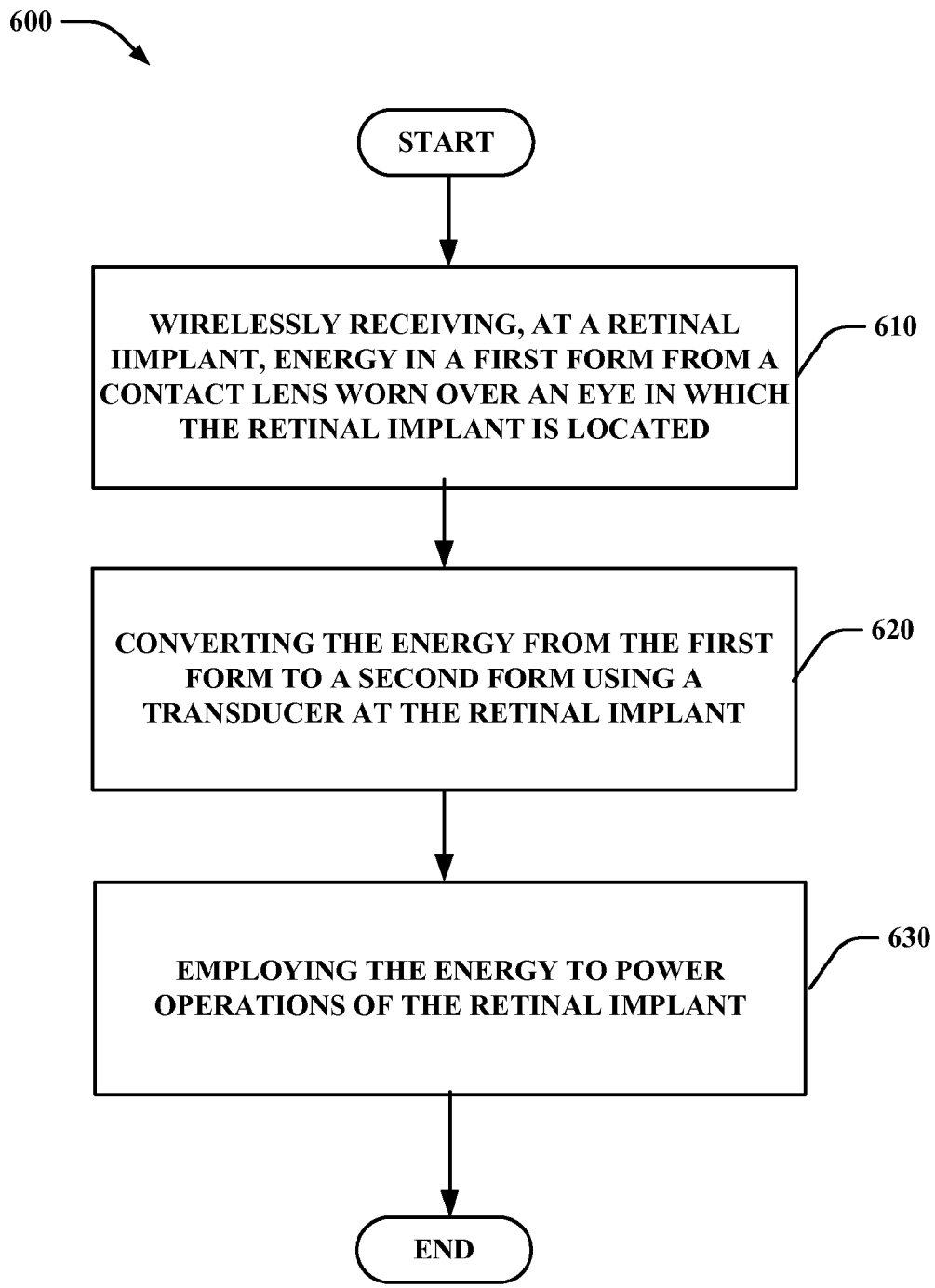
FIG. 6 is an exemplary flow diagram of a method for receiving energy from a contact lens in accordance with aspects described herein.

FIGS. 5-6 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Referring now to FIG. 5, presented is a flow diagram of an example application of systems and apparatuses disclosed in this description in accordance with an embodiment. In an aspect, in exemplary methodology 50, a contact lens such as those described herein (e.g. 102 and the like) is employed to transmit energy to a remote device. At 510, energy is received at a contact lens worn over an eye from an external power source. The energy is received in a first form (e.g. using power harvesting component 202). At 520, the energy is converted from the first form to a second form using a transducer disposed on or within the contact lens (e.g. using power harvesting component 202, energy transfer component 204, and/or circuitry 208). At 530, energy is transmitted in the second form to a device remote from the contact lens using an energy transfer component disposed on or within the contact lens (e.g. using energy transfer component 204).

FIG. 6 presents another flow diagram of an example application of systems and apparatuses disclosed in this description in accordance with an embodiment. In an aspect, in exemplary methodology 600, a receiving device such as those described herein (e.g., 300 and the like) is employed to wirelessly received energy transmitted from a contact lens. At 610, energy is wirelessly received at a retinal implant. The energy is received in a first form from a contact lens worn over an eye in which the retinal implant is located (e.g. using energy receiving component 302). At 620, the energy is converted from the first form to a second form using a transducer at the retinal implant (e.g. using energy transducer component 304). At 630, the energy is employed to power operations of the retinal implant (e.g. using circuitry 308).

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result.

Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens configured to be worn over an eye, comprising:
   a substrate that forms at least part of a body of the contact lens; and
   a circuit disposed on or within the substrate comprising:
      a power harvesting circuit component operatively coupled to an external power source, the power harvesting circuit component comprising a power transducer having one or more transducer elements, each of the one or more transducer elements being at least one of a solar power cell, a micro-electro-mechanical system, a radio frequency (RF) receiver, or an induction coil;
      an energy storage circuit component operatively coupled to the power harvesting circuit component, the energy storage circuit component comprising one or more storage elements, each of the one or more storage elements being at least one of a battery or a capacitor; and
      an energy transfer circuit component operatively coupled to at least one of the energy storage circuit component or the power harvesting circuit component, and wirelessly coupled to a self-contained device remote from the contact lens, the self-contained device comprising a receiver for wirelessly receiving power, and the energy transfer circuit being for wireless transmission of power from the contact lens to the self-contained device, the energy transfer circuit comprising one or more wireless transfer elements, each of the wireless transfer elements being one of an RF transmitter, an induction coil for direct or resonant inductive energy transfer, or an RF power amplifier.

2. The contact lens of claim 1, wherein the self-contained device is an implant configured to be integrated on or within part of the eye.

3. The contact lens of claim 1, wherein the energy transfer circuit component includes a RF antenna.

4. The contact lens of claim 3, wherein the power harvesting circuit component includes a converter to harvest mechanical energy generated with eye or eyelid movement.

5. The contact lens of claim 3, wherein the power harvesting circuit component includes a converter to harvest thermal energy.

6. The contact lens of claim 3, wherein the power harvesting circuit component includes a converter to harvest acoustic energy.

7. The contact lens of claim 3, wherein the power harvesting circuit component includes a converter to harvest chemical energy.

8. The contact lens of claim 3, wherein the power harvesting circuit component includes a converter to harvest radio frequency energy.

9. The contact lens of claim 1, wherein the inductive energy transfer uses a predetermined resonance frequency.

10. The contact lens of claim 9, wherein the power harvesting circuit component includes a converter to harvest mechanical energy generated with eye or eyelid movement.

11. The contact lens of claim 9, wherein the power harvesting circuit component includes a converter to harvest thermal energy.

12. The contact lens of claim 9, wherein the power harvesting circuit component includes a converter to harvest acoustic energy.

13. The contact lens of claim 9, wherein the power harvesting circuit component includes a converter to harvest chemical energy.

14. The contact lens of claim 9, wherein the power harvesting circuit component includes a converter to harvest radio frequency energy.

* * * * *